United States Patent
Bessonette et al.

(10) Patent No.: US 6,844,299 B2
(45) Date of Patent: Jan. 18, 2005

(54) POLYOL ESTER DERIVATIVES OF POLYAMINES AND USE IN TURBINE OILS TO IMPROVE CLEANLINESS

(75) Inventors: Paul W. Bessonette, Sarnia (CA); Patrick E. Godici, Naperville, IL (US); Kim E. Fyfe, Sarnia (CA); Jeenok T. Kim, Fairfax, VA (US)

(73) Assignee: BP Corporation North America Inc., Warrenville, IL (US)

( * ) Notice: Subject to any disclaimer, the term of this patent is extended or adjusted under 35 U.S.C. 154(b) by 108 days.

(21) Appl. No.: 10/370,427

(22) Filed: Feb. 20, 2003

(65) Prior Publication Data

US 2003/0228986 A1 Dec. 11, 2003

Related U.S. Application Data

(60) Provisional application No. 60/364,190, filed on Mar. 13, 2002.

(51) Int. Cl.[7] ................... C10M 133/16; C10M 159/12; C07D 233/36
(52) U.S. Cl. ................. 508/239; 508/240; 508/242; 508/454; 508/476; 508/477; 544/168; 544/399; 544/400; 560/169; 564/199
(58) Field of Search ................ 508/476, 477, 508/239, 240; 560/169; 544/168, 399, 400

(56) References Cited

U.S. PATENT DOCUMENTS

| | | | |
|---|---|---|---|
| 5,069,684 A | 12/1991 | Blain et al. | 44/331 |
| 5,275,748 A | * 1/1994 | Emert et al. | 508/239 |
| 5,397,489 A | * 3/1995 | Carlisle | 508/494 |

FOREIGN PATENT DOCUMENTS

| | | |
|---|---|---|
| EP | 0899324 A1 | 3/1999 |
| WO | WO9623855 | 8/1996 |

* cited by examiner

*Primary Examiner*—Ellen M. McAvoy
(74) *Attorney, Agent, or Firm*—Jennifer M. Hall

(57) ABSTRACT

This invention generally relates to new polyol ester derivatives of polyamines for use as dispersant additives compatible in synthetic ester-based turbo oils. The dispersant additives of the present invention consist of a hydrocarbon acid, a polyol, an amine carrier such as diacid or cyclic anhydride and a polyamine. The hydrocarbon acid makes up the non-polar hydrocarbon portion of the dispersant and the polyamine functions as the polar headgroup. The diacid or cyclic anhydride provides a means for attaching the polar polyamine to the dispersant structure through an amide linkage. Different dispersant structures are obtained by varying the hydrocarbon acid, the polyol and the nature of the polyamine.

63 Claims, 1 Drawing Sheet

Figure 1:
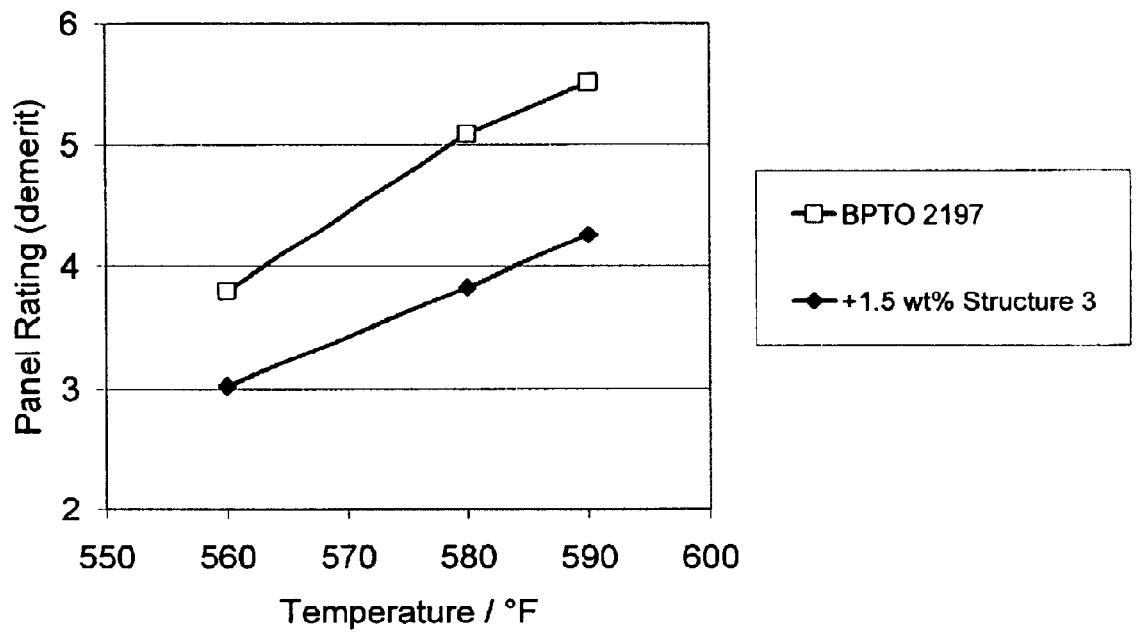

Deposit Rating - Inclined Panel Deposit Test

POLYOL ESTER DERIVATIVES OF POLYAMINES AND USE IN TURBINE OILS TO IMPROVE CLEANLINESS

CROSS-REFERENCE TO RELATED APPLICATIONS

This application claims priority from U.S. Provisional Application 60/364,190, filed Mar. 13, 2002 which is incorporated by reference herein.

FIELD OF THE INVENTION

This invention generally relates to new polyol ester derivatives of polyamines and their use as dispersant additives compatible in synthetic ester-based turbo oils. Aviation turbine oils containing the synthesized dispersant additives exhibit superior cleanliness by providing improved deposit control performance.

BACKGROUND OF THE INVENTION

Organic compositions, such as mineral oils and lubricating compositions, are subject to deterioration by oxidation and in particular are subject to such deterioration at high temperatures in the presence of air. This deterioration often leads to buildup of insoluble deposits that can foul engine parts, deteriorate performance, and increase maintenance. This is particularly the case for lubricating oils used in jet aircraft where wide temperature ranges and extreme operating conditions are likely to be encountered. Proper lubricating of aircraft gas turbines, for example, requires ability to function at bulk oil temperatures from as low as −60° C. to as high as 230°–280° C. Such an extreme temperature range places unique demands on the characteristics of the lubricant. Aviation jet turbine lubricants require superior thermal and oxidative stability, good viscosity-temperature characteristics (high VI), low volatility and a low pour point. Organic hydrocarbon-based oils are typically not robust enough to satisfy these requirements. Thus, aviation applications have relied on the superior performance characteristics of synthetic ester lubricants.

Ester base lubricating oil compositions prepared from polyols such as neopentyl glycol, trimethylolpropane or pentaerythritol, and a mixture of fatty acids and containing selected additive combinations are well known. These lubricants are functional over a wide temperature range and exhibit good thermal and oxidative stability. An ester base lubricant composition that will operate under more severe conditions, however, is a major goal of lubricant manufacturers. This invention addresses that continuing need by synthesizing dispersants that are compatible with synthetic ester base stock and which will improve the deposit control performance of the lubricant.

Conventional dispersants are oil-soluble additives that improve the deposit control performance of a lubricant by suspending deposit-forming precursors in the oil. These additives typically have a molecular structure consisting of a large non-polar hydrocarbon portion connected to a polar headgroup with the polar headgroup being comprised of nitrogen- and/or oxygen-containing functional groups. Dispersants solubilize deposit-forming precursors by incorporating the precursor into a micelle, with the polar component of the dispersant interacting with the deposit and the non-polar portion interacting with the surrounding oil. This interaction keeps the potentially harmful deposit precursors suspended.

Dispersants are critical to deposit control in gasoline and diesel crankcase lubricants and are often referred to as PIBSA-PAM type dispersants (PolyIsoButenyl Succinic Anhydride-PolyAMine). Many patents involve the use of PIBSA-PAM-type dispersant chemistry.

U.S. Pat. No. 4,655,946 to Exxon Research and Engineering discloses the use of very low levels of PIBSA-PAM dispersant in a sea water resistant turbo oil.

U.S. Pat. No. 3,914,179 to BP discloses the use of an amine with up to 24 carbon atoms in synthetic ester base stocks of the polyol type.

U.S. Pat. No. 4,253,980 to Texaco discloses a dicarboxylic acid ester lactone with pyridinium function on the ester. The pyridinium function uses a salt of halide, carbonate, sulphite, borate, carboxylate or phosphate as the counter ion to produce a quaternary ammonium salt.

U.S. Pat. No. 4,239,636 to Exxon Research and Engineering discloses functionalized pentaerythritol esters incorporating polar functional groups containing sulfur.

Conventional dispersants are not practical in aviation turbine lubricant formulations because they are synthesized in a mineral oil base stock. Mineral oil base stock is inherently less stable and would contaminate the aviation turbine oil product. In addition, they demonstrate poor miscibility with ester base stocks. Thus, Applicants have designed and synthesized dispersant additives that are compatible in ester base stocks. These dispersant additives, when added to a synthetic ester base stock turbo oil enhance the cleanliness of the turbo oil.

SUMMARY OF THE INVENTION

The present invention is a novel dispersant additive that is compatible with synthetic ester base stock, and a turbo oil composition containing this additive that exhibits enhanced cleanliness. The introduction of hotter, more efficient turbine engines require aviation turbine oils that will operate under more severe conditions. Turbine oils with improved high temperature cleanliness are necessary to operate in these more efficient engines. The novel dispersant additives of the present invention, when added to commercial turbine oil compositions, suspend deposit-forming precursors in solution and provide the improved high-temperature cleanliness performance needed.

The fundamental structure of the novel dispersant additives of the present invention comprises a hydrocarbon acid, a polyol, an amine carrier such as diacid or cyclic anhydride and a polyamine. The diacid or cyclic anhydride provides a means for attaching the polar polyamine to the dispersant structure through an amide linkage and will hereinafter be referred to as an amine carrier. Different dispersant structures are obtained by varying the hydrocarbon acid, the polyol and the nature of the polyamine. To enhance compatibility, the polyol used in the dispersant ester preferably is one of the polyols that are typically used in synthetic ester base stocks, i.e. neopentyl glycol, trimethylolpropane or pentaerythritol.

The various dispersant additive structures obtained in accordance with the invention, may be blended with a synthetic ester base stock, and optionally other additives, to provide a turbo oil composition with improved cleanliness.

DETAILED DESCRIPTION OF THE INVENTION

The dispersants of the present invention are useful in ester fluids including lubricating oils, particularly those ester fluids useful in high temperature aviation derived turbine engine oil applications. The dispersants exhibit improved deposit inhibiting performance as measured by the Inclined Panel Deposition Test. Total Acid Number (TAN) and viscosity increase of the lubricating oils containing these dispersants are also improved.

The dispersant additives of the invention comprise a hydrocarbon carboxylic acid, a polyol such as neopentyl glycol or pentaerythritol, an amine carrier such as succinic anhydride, and a polyamine. The figure below, shown in schematic form, represents the general embodiment of the present invention.

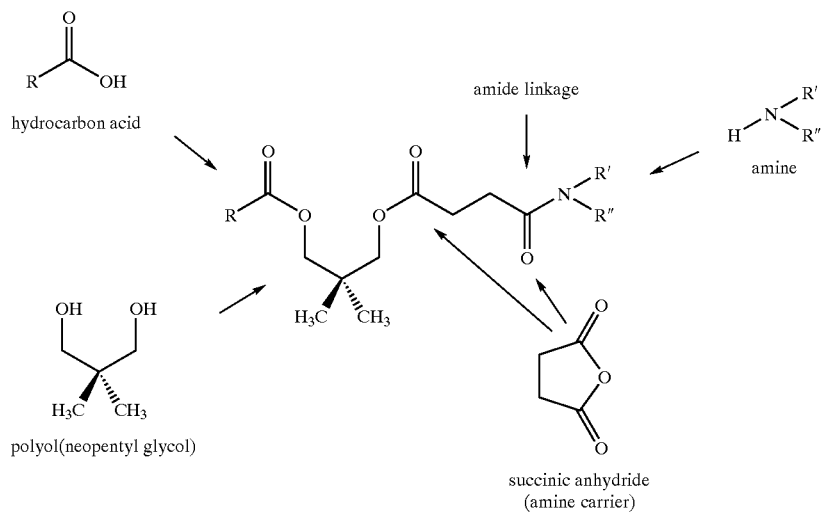

Different dispersant structures are obtained by varying the hydrocarbon carboxylic acid, the polyol and the polyamine. In addition, any diacid or cyclic anhydride can act as the amine carrier so long as it does not affect the solubility of the overall dispersant molecule.

Preferably, any polyol containing 2–4 OH groups with no hydrogen atoms on the beta-carbon atom can be used, i.e., any compound with the structure

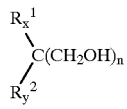

wherein x and y are, independently, 0 or 1 and n=4−(x+y). $R^1$ and $R^2$ are, independently, suitably a hydrocarbyl group, more particularly any aromatic, aliphatic or cyclo-aliphatic hydrocarbyl group, preferably an alkyl. The hydrocarbyl group may contain 1 to about 20 or more carbon atoms, and the hydrocarbyl group may also contain substituents such as chlorine, nitrogen and/or oxygen atoms. The hydrocarbyl group may contain one or more oxyalkylene groups and, thus, the polyol compounds include compounds such as polyetherpolyols (compounds having multiple ether linkages and multiple hydroxyl groups). The number of carbon atoms (i.e., carbon number, wherein the term carbon number as used throughout this application refers to the total number of carbon atoms in either the acid or alcohol as the case may be) and number of hydroxy groups (i.e., hydroxyl number) contained in the polyol compound used to form the carboxylic esters may vary over a wide range.

The following alcohols are particularly useful as polyols: neopentyl glycol, 2,2-dimethylol butane, 2,2-dimethyl-1,3-propanediol, trimethylol ethane, trimethylol propane, trimethylol butane, mono-pentaerythritol, technical grade pentaerythritol, di-pentaerythritol, tri-pentaerythritol. The most preferred alcohols are technical grade (e.g., approximately 88% mono-, 10% di- and 1–2% tri-pentaerythritol) pentaerythritol, monopentaerythritol, di-pentaerythritol, neopentyl glycol and trimethylol propane.

Preferably, but not necessarily, the choice of polyol in the dispersant structure is equivalent to the polyol base stock in which the dispersant will be blended. More preferably, the choice of polyol in the dispersant structure is directed by two factors: cost and the necessity of high-temperature stability.

Superior high-temperature performance is achieved if the carbon atoms at the beta position—relative to all of the alcohol groups in the polyol—are not attached to any hydrogen atoms. The preferred polyols used in Aviation Turbine Oil (ATO) base stocks are neopentyl glycol ("NPG") (n=2; $R_1$=CH$_3$; $R_2$=CH$_3$), trimethylolpropane ("TMP") (n=3; $R_1$=CH$_2$CH$_3$), and pentaerythritol ("PE") (n=4). All of these polyols have no beta hydrogen atoms and are commercially available, cost effective and are the most preferred polyols of the present invention. Neopentyl glycol only has two OH groups to react with the polar dispersing group and/or esterified with the hydrocarbon chain. Trimethylolpropane has three OH groups which can react with the amine carrier and then the polar polyamine and/or be esterified with hydrocarbon acids to form the dispersant structure. Pentaerythritol has four OH groups which can react with the amine carrier and then the polar polyamine and/or be esterified with hydrocarbon acids to form the dispersant structure. These hydrocarbon acids can be the same acid or a mixture of different acids.

In the overall formulation, however, it is likely that there will be a mixture of compounds comprising the dispersant. If Pentaerythritol (PE) is used as the polyol, for example, in one PE molecule all four of the hydroxyl groups may react with hydrocarbon acid chains while in another, perhaps only two or three of the four hydroxyl groups will react with hydrocarbon chains while the others will react with the polar dispersing (amine carrier/amine) group. Thus, another aspect of this invention is that the polyol—whether TMP, PE, NPG, or any other suitable polyol—can be partially esterified to achieve a mixed ester with any number of free hydroxyl groups available to react with the amine carrier and amine group. In other words, one can synthesize a polyol ester composition from a polyol and a hydrocarbon acid mixture in such a way that it has a substantial amount or a lesser amount of unconverted hydroxyl groups. The number of unconverted hydroxyl groups can be calculated and the mixed ester is given a hydroxyl number. The dispersant compound is then synthesized from the polyol ester, the amine carrier and amine group. Thus, the dispersant can be synthesized from a mixed ester having a wide range of hydroxyl groups available for reaction with the amine portion of the compound. A polyol ester with a lower hydroxyl number will have fewer unconverted hydroxyl groups available to react with the amine portion. This will result in a dispersant compound with fewer amine groups, and, fewer dispersant active nitrogen atoms. If the dispersant compound is synthesized from a polyol ester with a higher hydroxyl number (more commonly known as a high hydroxyl ester or HHE) more hydroxyl groups are available to react with the amine group and the dispersant compound produced, depending on the amine group used, can have greater dispersant properties. Starting with a polyol ester of a particular hydroxyl number provides flexibility so that the dispersant additive may be tailor made for the optimal amount of dispersant activity for a particular application. Alternatively, the present invention may be used to synthesize a polyol ester base stock with dispersant properties. This may be accomplished by starting with a polyol ester base stock with low hydroxyl number, reacting the base stock with an optimal amount of the amine carrier and amine group to form a complete base stock with an overall dispersant effect so that a separate dispersant additive is not needed.

Solubility in the base stock is an important factor that must be considered in the design of any additive. The ester base stock of ATOs is intermediate in polarity and, therefore, the dispersant additives of the present invention are preferably synthesized to have similar polarity to obtain reasonable solubility. An increase in the number of carbon atoms in the hydrocarbon acid portion of the molecule tends to make it more non-polar, while an increase in the number of polar groups in the amine will increase the overall polarity of the final molecule. Both of these factors must be considered in tandem to design a dispersant molecule that has the desired solubility properties.

Thus, any hydrocarbon carboxylic acid containing up to about 50 carbon atoms may be used, including those with a linear structure, branched, and/or with cyclic or aromatic components. Preferably linear, branched, cyclic, or aromatic acids with less than or equal to 18 carbon atoms are used because they are commercially available at a reasonable cost. Examples of branched acids include: 2,2-dimethyl propionic acid (neopentanoic acid), neoheptanoic acid, neooctanoic acid, neononanoic acid, hexanoic acid, isohexanoic acid, neodecanoic acid, 2-ethyl hexanoic acid (2EH), isoheptanoic acid, isooctanoic acid, isononanoic acid, and isodecanoic acid. Some examples of linear acids include acetic, propionic, pentanoic, heptanoic, octanoic, nonanoic, and decanoic acids. Selected polybasic acids include any $C_2$ to $C_{12}$ polybasic acids, e.g., adipic, azelaic, sebacic and dodecanedioic acids. And most preferably stearic acid, isononanoic acid, valeric acid, isovaleric, caproic, cyclohexanoic, benzoic, hexanoic acid, heptanoic acid, octanoic acid, nonanoic acid, and decanoic acid are used. Two hydrocarbon carboxylic acids that were readily available—stearic acid (18 carbon atoms) and isononanoic acid (9 carbon atoms)—were used in the neopentyl glycol Examples 1–14 below.

A variety of polyamines may be used when synthesizing the dispersant molecule. The amine moieties are linked to the molecular structure of the dispersant through an amide linkage to the amine carrier. Thus, any primary or secondary amine containing up to 10 nitrogen atoms could be used as the polyamine in the dispersant structure. Preferably, amines containing 2 to 5 nitrogen atoms chosen from the amine groups polyamines, piperazines, morpholines, anilines, piperidines, and pyrrolidines. Most preferably: 1-methylpiperazine, 1-(2-aminoethyl) piperazine, 1,4-bis(3-aminopropyl) piperazine, 4-(2-aminoethyl) morpholine, N-(3-aminopropyl)-1,3-propanediamine, N,N'-bis(3-aminopropyl) ethylenediamine, ethylenediamine, diethylenetriamine, triethylenetetramine, tetraethylenepentamine.

However, for every molecule synthesized according to the present invention, there is an upper limit to the number of active nitrogen atoms that can be feasibly incorporated into the final dispersant. The polarity of the final molecule will increase with an increase in the number of polar groups to the point where the dispersant would be incompatible in the ester base stock, and sufficient solubility would not occur.

The polar nitrogen-containing functional group is introduced into the overall dispersant molecule through attachment to one of the OH groups of the polyol mediated by an amine carrier. In general, any diacid or cyclic anhydride could potentially be used as the amine carrier. Preferably, commercially available diacids that contain up to 16 carbon atoms or cyclic anhydrides with 4 or 5 carbon atoms in the ring are used. Most preferably: succinic anhydride, maleic anhydride, glutaric anhydride, malonic acid, succinic acid, maleic acid, glutaric acid are used.

In order to synthesize the novel dispersants of the present invention a synthetic procedure was devised. Given the generalized structure of the disclosed dispersants (shown above), three major steps were required to synthesize the dispersants: (1) esterify carboxylic acid(s) to the polyol leaving at least one free OH group, (2) esterify free OH group on the polyol with a diacid or cyclic anhydride (amine carrier), and (3) attach the polyamine to a carboxylic acid group from the diacid or cyclic anhydride through an amide linkage.

Thus the building blocks of the molecular framework of the desired dispersant compounds can be represented by the following general schematic:

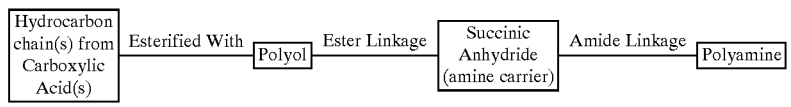

Two possible routes for the synthesis of these molecules were envisioned although one skilled in the art may synthesize the dispersant molecule in a different manner. In one scheme, the chosen carboxylic acid was esterified with the polyol in the presence of a catalytic amount of p-toluenesulfonic acid (Step 1). In the second step, the ester/alcohol product from Step 1 was reacted with the amine carrier, succinic anhydride, to form a second ester linkage with a carboxylic acid group at one end. In the final step, the carboxylic acid group was activated through the formation of a mixed anhydride using ethyl chloroformate at low temperature. The mixed anhydride was reacted with the desired polar amine entity to form an amide linkage, and the final product.

First Synthetic Scheme

Step 1

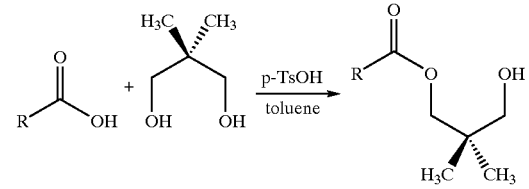

Step 2

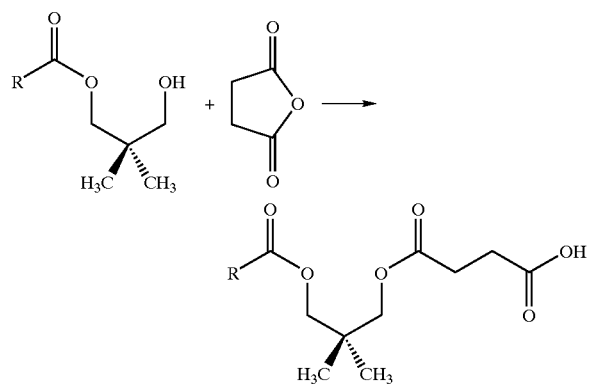

Step 3

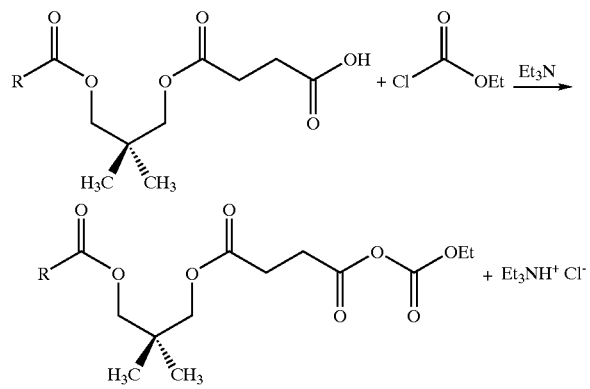

Step 4

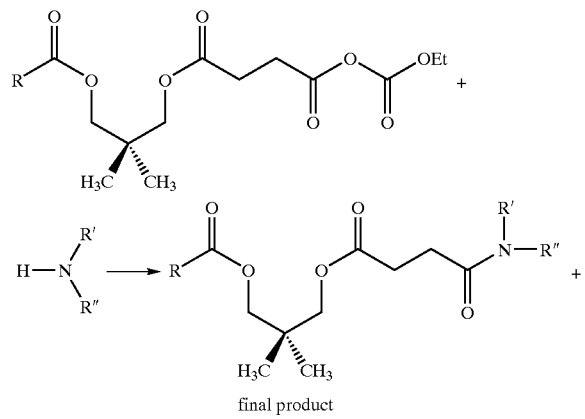

final product

In the second possible synthetic scheme, the amine group was reacted with the amine carrier, succinic anhydride, to form an amide with a free carboxylic acid group at one end. Esterification with a free hydroxyl group on the polyol gave the desired product.

Second Synthetic Scheme

Step 1

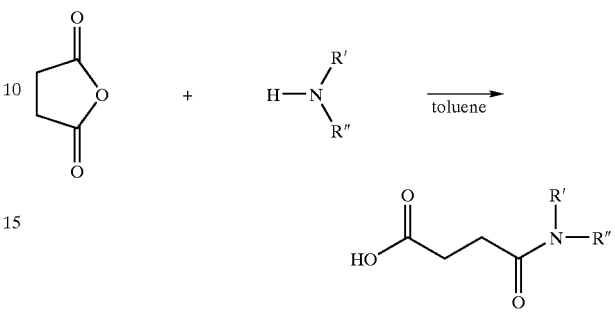

Step 2

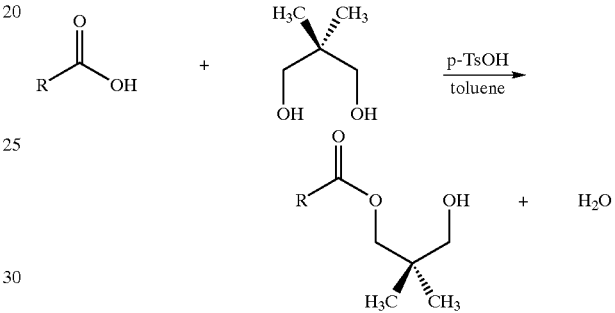

Step 3

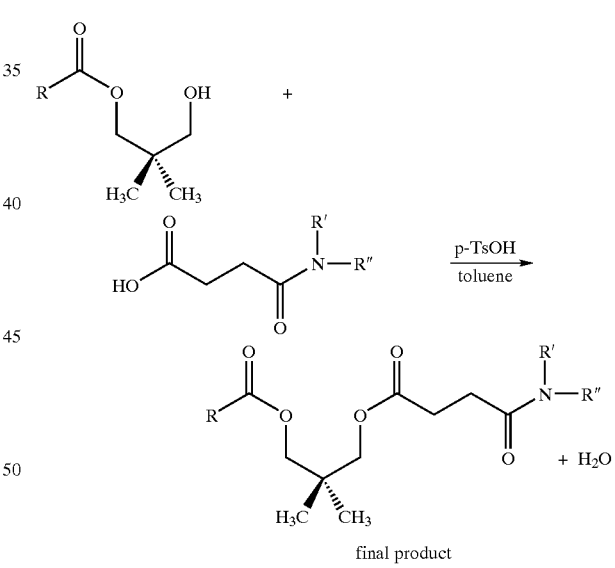

final product

The first scheme is preferred for the molecules containing the isononanoic acid group, while the second scheme is preferred for the synthesis of the structures containing a stearic acid group.

The dispersant additive of the present invention is combined with polyol ester base stocks to form the lubricant composition of the present invention. Preferably, the polyol from which the base stock is synthesized comprises 4 to 7 carbon atoms and 2 to 4 esterifiable hydroxyl groups. The aliphatic polyol may be selected from: neopentyl glycol, 2,2-dimethylol butane, trimethylol ethane, trimethylol propane, trimethylol butane, mono-pentaerythritol, technical grade pentaerythritol, di-pentaerythritol, tri-pentaerythritol, and neopentyl glycol. Preferred polyols are technical grade pentaerythritol (e.g., approximately 88% mono-, 10% di- and 1–2% tri-pentaerythritol), monopentaerythritol, di-pentaerythritol, neopentyl glycol, trimethylol propane, and tripentaerythritol. More preferred polyols are selected from: trimethylolpropane, technical grade pentaerythritol, monopentaerythritol, dipentaerythritol, neopentyl glycol, and tripentaerythritol. Even more preferred polyols are selected from technical grade pentaerythritol, trimethylolpropane, and neopentyl glycol.

A preferred polyol is Technical pentaerythritol (TechPE). Technical pentaerythritol is a mixture that includes about 85 to 92 wt % monopentaerythritol and 8 to 15 wt % dipentaerythritol. A typical commercial technical pentaerythritol contains about 88 wt % monopentaerythritol and about 12 wt % of dipentaerythritol. The technical pentaerythritol may also contain some tri and tetra pentaerythritol which are typically formed as by-products during the production of technical pentaerythritol.

The preferred polyol ester base stock contains a mixture of $C_{5-10}$ acids. Even more preferably, the acids are a mixture of $C_5$, i-$C_9$, and linear $C_{7-10}$ acids. It is noted that $C_{7-10}$ is intended to represent a mixture of $C_7$, $C_8$, $C_9$, and $C_{10}$ acids. Preferably, this mixture acid) acids.

The lubricant composition of the present invention preferably has at least one of the following uses: crankcase engine oils, two-cycle engine oils, catapult oils, hydraulic fluids, drilling fluids, turbine oils (e.g., aircraft turbine oils), greases, compressor oils, gear oils and functional fluids. Preferably, the lubricant composition of the present invention is used in an aero-derived, gas turbine engines (e.g., jet turbine engines, marine engines, and power generating applications).

The lubricant composition according to the present invention preferably comprises about 90 to 99.5% by weight of the polyol ester base stock and about 0.5 to 10 wt %, preferably about 1 to 5% by weight of the novel dispersant additive.

In addition to the synthesized dispersant additive, the lubricant compositions of the present invention may also comprise other conventional lubricant additives. Lubricating oil additives are described generally in "Lubricants and Related Products" by Dieter Klamann, Verlag Chemie, Deerfield, Fla., 1984, and also in "Lubricant Additives" by C. V. Smalheer and R. Kennedy Smith, 1967, pp. 1–11, the contents of which are incorporated herein by reference. Lubricating oil additives are also described in U.S. Pat. Nos. 6,043,199, 5,856,280, and 5,698,502, the contents of which are incorporated herein by reference.

Conventional lubricants preferably comprise about 0 to 15%, preferably 2 to 10 wt %, most preferably 3 to 8% by weight of a lubricant additive package. Thus, the lubricant composition according to the present invention would comprise about 85 to 97 wt % polyol ester base stock, about 2 to 10 wt % conventional additive package and about 1 to 5 wt % of the novel dispersant additive of the present invention.

Thus, fully formulated turbine oils may contain one or more of the following classes of additives: antioxidants, antiwear agents, extreme pressure additives, antifoamants, detergents, hydrolytic stabilizers, metal deactivators, other rust inhibitors, etc. in addition to the dispersant of the present invention. Total amounts of such other additives can be in the range 0.5 to 15 wt % preferably 2 to 10 wt %, most preferably 3 to 8 wt % of the fully formulated lubricant.

Antioxidants, which can be used, include aryl amines, e.g. phenylnaphthylamines and dialkyl diphenylamines and mixtures thereof, hindered phenols, phenothiazines, and their derivatives. The antioxidants are typically used in an amount in the range 1 to 5 wt % of the fully formulated lubricant.

Antiwear/extreme pressure additives include hydrocarbyl phosphate esters, particularly trihydrocarbyl phosphate esters in which the hydrocarbyl radical is an aryl or alkaryl radical or mixture thereof. Particular antiwear/extreme pressure additives include tricresyl phosphate, triaryl phosphate, and mixtures thereof. Other or additional anti wear/extreme pressure additives may also be used. The antiwear/extreme pressure additives are typically used in an amount in the range 0 to 4 wt %, preferably 1 to 3 wt % of the fully formulated lubricant.

Industry standard corrosive inhibitors may also be included in the turbo oil. Such known corrosion inhibitors include the various triazols, for example, tolyltriazol, 1,2,4 benzotriazol, 1,2,3 benzotriazol, carboxy benzotriazole, allylated benzotriazol. The standard corrosion inhibitor additive can be used in an amount in the range 0.02 to 0.5 wt %, preferably 0.05 to 0.25 wt % of the fully formulated lubricant. Other rust inhibitors common to the industry include the various hydrocarbyl amine phosphates and/or amine phosphates.

Foam control can be provided by many compounds including an antifoamant of the polysiloxane type, e.g., silicone oil or polydimethyl siloxane.

Another additive that can be used is an anti-deposition and oxidative additive. A typical anti-deposition and oxidation additive is a sulfur containing carboxylic acid (SCCA) as range 100 to 2000 ppm, preferably 200 to 1000 ppm, most preferably 300 to 600 ppm.

As previously indicated, other additives can also be employed including hydrolytic stabilizers, pour point depressants, anti foaming agents, viscosity and viscosity index improver, as well as other additives useful in lubricating oil compositions.

The individual additives may be incorporated into the present lubricant composition in any convenient way. Thus, each of the components can be added directly to the base stock by dispersing or dissolving it in the base stock at the desired level of concentration. Such blending may occur at ambient temperature or at an elevated temperature. Preferably, all the additives except for the viscosity modifier and the pour point depressant are blended into a concentrate or additive package, which is subsequently blended into base stock to make finished lubricant. Use of such concentrates is this manner is conventional. The concentrate will typically be formulated to contain the additive(s) in proper amounts to provide the desired concentration in the final formulation when the concentrate is combined with a predetermined amount of base lubricant. The concentrate is preferably made in accordance with the method described in U.S. Pat. No. 4,938,880, the contents of which are incorporated herein by reference. That patent describes making a pre-mix of ashless dispersant and metal detergents that is pre-blended at a temperature of at least about 100° C. Thereafter, the pre-mix is cooled to at least 85° C. and the additional components are added.

The present invention is further described by reference to the following non-limiting examples. These examples are provided for purposes of explanation and not limitation. Specific polyols, carbon acids and polyamines and synthetic procedures are used to synthesize the novel dispersant in order to provide a thorough understanding of the present invention. However, it will be apparent to one skilled in the art that the present invention may be practiced in other embodiments that depart from these specific examples. The examples illustrate the use of neopentyl glycol and pentaerythritol as possible glycols, stearic acid and isononanoic acid as possible hydrocarbon acids for neopentyl glycol dispersants, various $C_5$–$C_{10}$ carboxylic acids for pentaerythritol dispersants and seven different polyamines as listed in Table 1.

The reaction mixture was reheated to boiling, and 0.15 moles of succinic anhydride were added to the hot solution, which was refluxed for 3 hours and afterwards allowed to cool naturally to room temperature and sit overnight.

The solution was cooled with a saturated salt water/ice bath and 0.15 mol of triethylamine were added dropwise

TABLE 1

Structures and names of the seven polyamines chosen for the dispersant compounds

| Structure | Amine Number |
|---|---|
| H₂NCH₂CH₂N⟨morpholine⟩O <br> 4-(2-aminoethyl)morpholine | Amine 1 |
| HN⟨piperazine⟩N—CH₃ <br> 1-methylpiperazine | Amine 2 |
| H₂NCH₂CH₂N⟨piperazine⟩NH <br> 1-(2-aminoethyl)piperazine | Amine 3 |
| H₂N~~~N⟨piperazine⟩N~~~NH₂ <br> 1,4-bis(3-aminopropyl)piperazine | Amine 4 |
| H₂N~~~NH~~~NH₂ <br> N-(3-aminopropyl)-1,3-propanediamine | Amine 5 |
| H₂N~~~NH~~~NH~~~NH₂ <br> N,N'-bis(3-aminopropyl)ethylenediamine | Amine 6 |
| H₂N~~NH~~NH~~NH~~NH₂ <br> tetraethylenepentamine | Amine 7 |

Synthesis of Neopentyl Glycol Dispersants

For the neopentyl glycol dispersant molecules, two carboxylic acids were chosen for the syntheses: stearic acid (linear 18-carbon acid) and isononanoic acid (3,5,5-trimethyl hexanoic acid; branched). Combining these two possibilities for the hydrocarbon portion with the seven possible polar polyamine groups shown in Table 1 gives fourteen potential candidates, all of which are described in the following Examples.

EXAMPLE 1

Synthesis of Polyol Ester Derivatives of Neopentyl Glycol, Succinic Anhydride, 4-(2-aminoethyl) morpholine and Stearic Acid Procedure: 0.15 moles of neopentyl glycol were esterified with 0.15 moles of stearic acid in toluene using p-toluenesulfonic acid as a catalyst. The apparatus was fitted with a Dean and Stark trap and heated to boiling for 8 hours, after which it was allowed to cool naturally to room temperature.

with stirring. 0.15 mol of ethyl chloroformate in 20 mL of methylene chloride were added dropwise with stirring to the cooled solution over a period of 15 minutes. The reaction was allowed to proceed cooled, stirred, and undisturbed for 2 hours. During this time, the solution turned light purple in color. 0.15 moles of 4-(2-aminoethyl)morpholine in 20 mL of methylene chloride were added dropwise with stirring to the cooled solution over a period of several minutes, and the mixture was stirred and cooled for 2 hours. The mixture was suction filtered and the solvent was discarded. The solid was removed from the filtrate using a rotary evaporator hooked up to a high vacuum pump and a dry ice/acetone trap. The viscous liquid remaining solidified on cooling to room temperature and standing overnight. A sample of the solid was submitted for IR analysis and the analysis was consistent with the proposed schematic structure illustrated above and will hereinafter be referred to as Structure 1.

EXAMPLES 2–14

A similar procedure was used to make fourteen neopentyl glycol dispersants in total. The fourteen structures are set forth in Table II below. To test for solubility of the neopentyl glycol additives, 50 g of a 1.5 wt % mixture of each individual additive in BPTO 2197, a commercially available jet turbine lubricant from Air BP, was prepared and heated to near 80° C. with stirring. The mixture/solution was then allowed to cool naturally to room temperature and sit covered and undisturbed for 24 hours. The solutions were then examined for clarity and insoluble particles.

If excessive cloudiness or insoluble particles were observed in the test solution after sitting undisturbed for 24 hours, the dispersant additive was deemed insoluble in the commercial lubricant, and the additive was not subjected to any further testing. If the synthesized dispersants were soluble in the commercial lubricant, they were given structure numbers for the purposes of the Inclined Panel Deposit Test (IPDT). For the most part, the compounds observed to be insoluble at these treat rates were the ones containing long-chain linear polyamines with four or five nitrogen atoms. The inclusion of a large number of polar nitrogen-containing functional groups in the molecular structure likely caused the compound to be too polar to dissolve in the synthetic ester base stock.

TABLE II

| Acid | Polyamine | Structure # | Soluble? |
| --- | --- | --- | --- |
| Stearic | Amine 1 | Structure 1 | ✓ |
| Stearic | Amine 2 | Structure 2 | ✓ |
| Stearic | Amine 3 | Structure 3 | ✓ |
| Stearic | Amine 4 | Structure 4 | ✓ |
| Stearic | Amine 5 | Insoluble | X |
| Stearic | Amine 6 | Insoluble | X |
| Stearic | Amine 7 | Insoluble | X |
| Isononanoic | Amine 1 | Structure 5 | ✓ |
| Isononanoic | Amine 2 | Structure 6 | ✓ |
| Isononanoic | Amine 3 | Structure 7 | ✓ |
| Isononanoic | Amine 4 | Structure 8 | ✓ |
| Isononanoic | Amine 5 | Structure 9 | ✓ |
| Isononanoic | Amine 6 | Structure 10 | ✓ |
| Isononanoic | Amine 7 | Insoluble | X |

Synthesis of Pentaerythritol Dispersants

Pentaerythritol dispersant candidates were synthesized from high hydroxyl pentaerythritol ester base stocks obtained from Exxon Chemical. In a high hydroxyl ester (HHE), most of the hydroxyl groups are esterified with a distribution of various carboxylic acids, but some of the hydroxyl groups are left unreacted. The number of unreacted hydroxyl groups is indicated by the hydroxyl number (effective mg KOH per gram ester) of the HHE base stock. These free hydroxyl groups can be functionalized with polar amine groups to form pentaerythritol dispersants, with the following general structure:

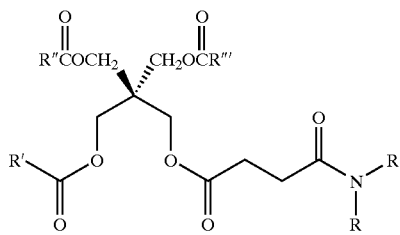

Two HHE basestocks were obtained from Exxon Chemical, which differ in the carboxylic acid distribution used to form the pentaerythritol esters. One basestock (referred to hereafter as HHE1) was composed of 84.9 mol % n-valeric acid and 15.1 mol % isononanoic acid with a hydroxyl number of 37.7. The carboxylic acid distribution of the second HHE basestock (HHE2) consisted of 51.56 mol % n-valeric acid, 0.74 mol % n-hexanoic acid, 25.20 mol % n-heptanoic acid, 8.71 mol % n-octanoic acid, 5.39 mol % n-decanoic acid, and 8.40 mol % isononanoic acid, with a hydroxyl number of 37.5.

EXAMPLE 15

Synthesis of High Hydroxyl Ester Dispersant Additive from High Hydroxyl Ester (pentaerythritol: n-valeric/isononanoic acid 84.9 mol %; 15.1 mol %; hydroxyl #: 37.7), succinic anhydride and 1-(2-aminoethyl)piperazine.

Procedure: 30.0 g of the high hydroxyl ester were placed in a round-bottomed flask with 50 mL of toluene and heated with stirring to 100° C. 2.02 g of succinic anhydride were added to the hot solution which was then refluxed for 4 hours, after which it was allowed to cool naturally to room temperature and sit overnight. The solution was cooled with a saturated salt water/ice bath and 2.8 mL (0.020 mol) of triethylamine were added dropwise with stirring. 1.9 mL (0.020 mol) of ethyl chloroformate in 10 mL of methylene chloride was added dropwise with stirring to the cooled solution over a period of 5 minutes. The reaction was allowed to proceed cooled, stirred and undisturbed for 2 hours. During this time the solution turned light purple in color. 2.6 mL (0.020 mol) of 1-(2-aminoethyl)piperazine in 50 mL of methylene chloride were placed in a separate cooled round-bottomed flask. The ethyl chloroformate/triethylamine mixture was added slowly to the cooled 1-(2-aminoethyl)piperazine solution, and the mixture was stirred and cooled for 2 hours. The mixture was suction filtered and the solid was discarded. The solvent was removed from the filtrate using a rotary evaporator hooked up to a high vacuum pump and a dry ice/acetone trap. Some solid came out of the resulting orange-colored liquid which was filtered and discarded. A sample of the filtrate was submitted for IR analysis and it was consistent with the proposed structure and will hereinafter be referred to as Structure 11.

EXAMPLE 16–20

A series of pentaerythritol dispersant candidates was synthesized from both of the HHE 1 and HHE 2 basestocks and several of the polyamines listed in Table 1 and are disclosed in Table 3. The synthetic procedure used to prepare these dispersant compounds was very similar to the procedure described above. For the pentaerythritol dispersants, detailed calculations revealed that a 4.5 wt % solution of pentaerythritol dispersant is approximately similar to a 1.5 wt % solution of neopentyl glycol dispersant, in terms of maintaining an equal number of moles of dispersant in the test solution. Therefore, solubility testing was performed on a 4.5 wt % mixture of each pentaerythritol dispersant in commercially available jet turbine lubricant from Air BP using the same procedure as described for the neopentyl glycol dispersants.

If excessive cloudiness or insoluble particles were observed in the test solution after sitting undisturbed for 24 hours, the dispersant additive was deemed insoluble in the commercially available jet turbine lubricant used, and the additive was not subjected to any further testing. If the synthesized dispersants were soluble in the commercial lubricant, they were given structure numbers for the purposes of the Inclined Panel Deposit Test (IPDT). For the most part, the compounds observed to be insoluble were the ones containing long-chain linear polyamines with four or five nitrogen atoms. The inclusion of a large number of polar nitrogen-containing functional groups in the molecular structure likely caused the compound to be too polar to dissolve in the synthetic ester base stock.

TABLE III

| Polyamine | High-Hydroxyl Ester | Structure# | Soluble? |
|---|---|---|---|
| Amine 1 | HHE1 | Not measured | ✓ |
| Amine 3 | HHE1 | Structure 11 | ✓ |
| Amine 4 | HHE1 | Structure 12 | ✓ |
| Amine 5 | HHE1 | Not measured | ✓ |
| Amine 6 | HHE1 | Insoluble | X |
| Amine 7 | HHE1 | Structure 13 | ✓ |
| Amine 1 | HHE2 | Not measured | ✓ |
| Amine 3 | HHE2 | Structure 14 | ✓ |
| Amine 4 | HHE2 | Structure 15 | ✓ |
| Amine 6 | HHE2 | Insoluble | X |
| Amine 7 | HHE2 | Insoluble | X |

EXAMPLE 21
Inclined Panel Deposit Test (IPDT)

The IPDT is generally used to predict field performance in the oil-washed areas of the engine, and successfully correlates with more expensive bearing rig tests. The IPDT is typically employed as a screener test for additives in base stocks and fully formulated lubricants.

Test Procedure

During the IPDT, the test oil flows at a rate of 60 mL/h over a heated panel (stainless steel 304) that is inclined at an angle of 4 degrees with respect to the horizontal. Moist air flows through the system continuously during the test at a rate of 12 L/h. The panel is heated to a specified temperature (up to 600° F.) which is held constant for the entire test duration of 24 hours. Oil flowing off the panel is collected in a sump and is continuously recirculated by a positive displacement pump.

When the test is complete, the deposit formed on the panel during the test is rated using a demerit rating scale. The IPDT uses the same deposit demerit system as the High Temperature Bearing Test. During the rating process, the total deposit is portioned into different deposit types, depending on the severity of the deposit. Each type of deposit is assigned a demerit factor related to the deposit severity. The demerit factor is multiplied by the area of the deposit type to obtain the demerits for that particular deposit type. The total number of demerits is then obtained by adding together the demerits for each deposit type. Dividing the total number of demerits by the total area of the deposits gives the final deposit demerit panel rating. Only the oil wetted areas of the panel are rated.

The used oil at the end of the test is subjected to total acid number (TAN) and viscosity analyses. The TAN is performed according to ASTM D664 (except to a pH=11.00 endpoint), and the viscosity measurement is performed at 40° C. according to ASTM D445.

For the soluble neopentyl glycol dispersant compounds, separate test formulations were prepared by dissolving 1.5 wt % of the additive in the commercial lubricant. Similar formulations were prepared from the soluble pentaerythritol dispersant additives, with the exception that each blend contained 4.5 wt % dispersant compound in the commercial lubricant.

The deposit control capability of each experimental formulation was tested by IPDT at three separate temperatures: 560° F., 580° F., and 590° F. Each test at a particular temperature was run in duplicate and the final results were averaged.

Figure 2:
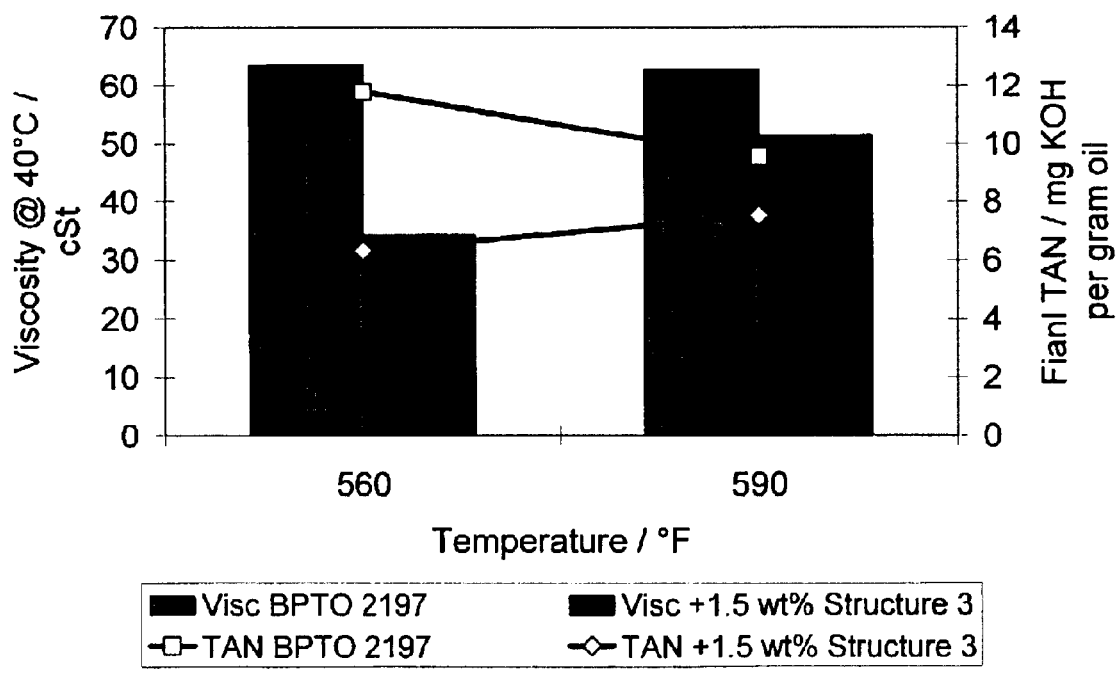

The IPDT results for dispersant additive structures 1–15 blended in BPTO 2197, a commercially available turbine oil from Air BP, are indicated in Table IV. The results are compared to IPDT results obtained for BPTO 2197 without dispersant additive. FIGS. 1 and 2 are two plots comparing the performance of BPTO 2197 alone and with 1.5 wt % of dispersant additive Structure 3. FIG. 1 compares IPDT panel demerit rating data, while FIG. 2 compares results from TAN and viscosity analyses of the used oil at the end of the test.

The IPDT results presented in Table IV show that for all of the new dispersant formulations, improved deposit control is obtained relative to the commercial lubricant at 560° F. and 580° F. and all but two show improved deposit control at 590° F. The dispersant blends containing Structures 3, 4, 8, 12, 13, and 15 show surprisingly improved cleanliness benefit compared to the commercial lubricant alone at all temperatures. FIGS. 1 and 2 are graphs depicting the improved Deposit rating and Viscosity and TAN Control for Structure 3.

TABLE IV

| Structure No. | Deposit Rating | | | Final TAN | | Final Viscosity | |
|---|---|---|---|---|---|---|---|
| BPTO 2197 plus | 560° C. | 580° C. | 590° C. | 560° C. | 590° C. | 560° C. | 590° C. |
| 1 (1.5%) | 2.7 | 4.7 | 5.3 | 0.9 | 5.3 | 29.0 | 64.0 |
| 2 (1.5%) | 3.3 | 5.0 | 5.4 | 3.6 | 7.7 | 33.9 | 46.8 |
| 3 (1.5%) | 3.0 | 3.8 | 4.3 | 6.3 | 7.5 | 34.6 | 51.5 |
| 4 (1.5%) | 2.8 | 3.8 | 4.9 | 0.5 | 7.0 | 28.8 | 40.8 |
| 5 (1.5%) | 2.6 | 4.6 | 5.7 | 1.2 | 7.6 | 29.2 | 50.1 |
| 6 (1.5%) | 2.8 | 5.0 | 5.9 | 0.8 | 10.9 | 28.6 | 50.8 |
| 7 (1.5%) | 3.3 | 4.6 | 5.4 | 3.7 | 8.5 | 30.9 | 54.1 |
| 8 (1.5%) | 3.0 | 3.7 | 4.5 | 1.2 | 6.6 | 32.8 | 37.7 |
| 9 (1.5%) | 3.7 | 5.0 | 5.2 | 5.4 | 10.4 | 33.4 | 53.5 |
| 10 (1.5%) | 3.5 | 4.4 | 5.2 | 3.3 | 11.0 | 32.9 | 55.9 |
| 11 (4.5%) | 2.4 | 4.8 | 4.5 | 1.6 | 8.2 | 30.8 | 70.4 |
| 12 (4.5%) | 2.4 | 3.5 | 4.2 | 0.5 | 9.7 | 28.7 | 46.1 |
| 13 (4.5%) | 2.1 | 3.7 | 3.8 | 2.0 | 5.1 | 32.7 | 46.1 |
| 14 (4.5%) | 3.3 | 4.4 | 5.1 | 4.8 | 7.0 | 31.4 | 41.3 |
| 15 (4.5%) | 2.3 | 3.6 | 3.9 | 1.2 | 5.6 | 30.4 | 45.4 |
| BPTO2197 | 3.8 | 5.1 | 5.5 | 11.8 | 9.6 | 63.7 | 62.9 |

Table IV roughly indicates that, all else being equal, an increase in the number of "active" dispersing nitrogen atoms in the dispersant structure appears to correlate with greater improvement in deposit control.

In addition, Tables II and III illustrate that there is an upper limit to the number of active nitrogen atoms that can be feasibly incorporated into the final dispersant without impacting the solubility of the dispersant in ester base stock. The polarity of the final dispersant molecule will increase with an increase in the number of polar groups to the point where the dispersant may be incompatible with the ester base stock, and solubility may not occur.

EXAMPLE 22
Coker Mister Experiments

The IPDT is traditionally used as a screener test. A more rigorous and extensive evaluation of the deposit forming tendency of turbine oils is provided by the coker mister test. This test is designed to simulate the hot section of a jet engine bearing compartment. It evaluates the tendency of synthetic aviation oils to form deposits in the liquid and vapor phases.

Test Procedure

During the coker mister test, a sample of the test oil is sprayed into a hot tube set at a specified temperature for the desired time period (usually 20 hours). The temperature of the tube is constant for a particular run, and is typically set in the range from 500° F. to over 600° F. Air flow through the system is maintained at 9 L/min and the oil flow rate is 20 mL/min. At the end of the test, the liquid, vapour, and endplate "wetted" portions of the coker mister tube are each individually rated using a similar demerit scale as used for the IPDT. The used oil is subjected to a viscosity measurement at 40° C. (according to ASTM D445) and a TAN analysis (ASTM D664; except to a pH=11.00 endpoint).

The dispersant additive formulation—Structure 6—was tested by the coker mister test. A formulation was blended containing 1.5 wt % of this dispersant additive dissolved in BPTO 2380. The results comparing BPTO 2380 with and without the dispersant additive are shown in Table V.

TABLE V

| Structure No. | Liquid Rating | | Vapor Rating | | End Plate Rating | | Final TAN | |
|---|---|---|---|---|---|---|---|---|
| Temp ° F. | 570 | 590 | 570 | 590 | 570 | 590 | 570 | 590 |
| BPTO 2380 with 1.5% Structure 6 | 6.3 | 7.8 | 4.6 | 7.8 | 7.0 | 9.0 | 6.1 | 17.8 |
| BPTO 2380 | 7.8 | 8.9 | 7.7 | 9.9 | 9.8 | 10.2 | 15.5 | 24.8 |

Cleanliness improvement in all categories is observed in the dispersant formulation at both temperatures

We claim:

1. A dispersant for a lubricating oil, said dispersant comprising the reaction product of the following components:
   (i) at least one hydrocarbon carboxylic acid;
   (ii) at least one polyol or partially esterified polyol;
   (iii) at least one amine carrier selected from the group consisting of diacids and cyclic anhydrides; and
   (iv) at least one polyamine having up to 10 nitrogen atoms;
   wherein said hydrocarbon carboxylic acid and said polyol or partially esterified polyol react to form an ester linkage, and said at least one amine carrier and said at least one amine react to form an amide linkage.

2. The dispersant of claim 1 wherein said at least one polyol is selected from the group consisting of: neopentyl glycol, 2,2-dimethylol butane, trimethylol ethane, trimethylol propane, trimethylol butane, mono-pentaerythritol, di-pentaerythritol, and tri-pentaerythritol, and mixtures thereof.

3. The dispersant of claim 1 wherein said at least one polyamine is selected from the group consisting of: polyamines containing 2 to 5 nitrogen atoms, piperazines, morpholines, anilines, piperidines, and pyrrolidines, and mixtures thereof.

4. The dispersant of claim 1 wherein said at least one hydrocarbon carboxylic acid is selected from the group consisting of: linear, branched, cyclic, and aromatic acids having up to 18 carbon atoms, and mixtures thereof.

5. A lubricant composition exhibiting enhanced cleanliness, said lubricant composition comprising:
   a major portion of a polyol ester base stock; and
   a minor portion of the dispersant of claim 1.

6. A method of making a dispersant for a lubricating oil, said method comprising reacting the following components to form a reaction product:
   (i) at least one hydrocarbon carboxylic acid;
   (ii) at least one polyol or partially esterified polyol;
   (iii) at least one amine carrier selected from the group consisting of diacids and cyclic anhydrides; and
   (iv) at least one polyamine containing up to 10 nitrogen atoms, wherein the reaction product has an ester linkage attaching said hydrocarbon carboxylic acid to said polyol or partially esterified polyol, and an amide linkage attaching said amine carrier to said polyamine.

7. The method of claim 6 wherein said at least one amine carrier is succinic anhydride, and said at least one polyol is selected from the group consisting of: neopentyl glycol, trimethylolpropane, pentaerythritol and mixtures thereof.

8. The method of claim 6 wherein said at least one polyamine is selected from the group consisting of: 1-methylpiperazine, 1-(2-aminoethyl)piperazine, 1,4-bis(3-aminopropyl)piperazine, 4-(2-aminoethyl)morpholine, N-(3-aminopropyl)-1,3-propanediamine, N,N'-bis(3-aminopropyl)ethylenediamine, ethylenediamine, diethylenetriamine, triethylenetetramine, and tetraethylenepentamine, and mixtures thereof.

9. A lubricant composition exhibiting enhanced cleanliness, said lubricant composition comprising:
   a major portion of a polyol ester base stock; and
   a minor portion of the dispersant made by the method of claim 6.

10. A method for enhancing the cleanliness of a synthetic ester based turbo oil by adding to said turbo oil, in a dispersant effective amount, the dispersant made by the method of claim 6.

11. A dispersant additive having the structure X—R, wherein X is a functional group substituted by at least one of nitrogen and oxygen and R is an esterified or partially esterified polyol, and X and R are linked by an ester linkage, wherein said dispersant additive: (a) enhances the cleanliness of a synthetic ester base stock to which it is added, (b) is stable at temperatures greater than about 230° C.; and (c) is soluble at treat rates of up to about 10% in synthetic ester base stocks.

12. The dispersant additive of claim 11 wherein the dispersant additive comprises 2 to 5 nitrogen atoms.

13. The dispersant of claim 1 wherein said polyol or partially esterified polyol has the structure:

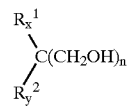

wherein x and y are, independently, 0 or 1, and n is 2, 3 or 4; and wherein $R^1$ and $R^2$ are, independently, hydrocarbyl groups; provided that:
   when n is 3, $R_2$ is not present in the structure, and
   when n is 4, $R_1$ and $R_2$ are not present in the structure.

14. The dispersant of claim 1 wherein said at least one hydrocarbon carboxylic acid is selected from the group consisting of: 2,2-dimethyl propionic acid, neoheptanoic acid, neooctanoic acid, neononanoic acid, hexanoic acid, iso-hexanoic acid, neodecanoic acid, 2-ethyl hexanoic acid, isoheptanoic acid, isooctanoic acid, isononanoic acid, isodecanoic acid, acetic acid, propionic acid, pentanoic acid, heptanoic acid, octanoic acid, nonanoic acid, decanoic acid, stearic acid, valeric acid, isovaleric acid, caproic acid, cyclohexanoic acid, and benzoic acid, and mixtures thereof.

15. The dispersant of claim 1 wherein said at least one polyamine contains a cyclic amine.

16. The dispersant of claim 1 wherein said at least one polyamine contains 2 or 3 nitrogen atoms.

17. The dispersant of claim 1 wherein said at least one polyamine is selected from the group of 1-methylpiperazine, 1-(2-aminoethyl) piperazine, 1,4-bis(3-aminopropyl) piperazine, 4-(2-aminoethyl) morpholine, and N-(3-aminopropyl)-1,3-propanediamine, and mixtures thereof.

18. The dispersant of claim 1 wherein said at least one amine carrier is selected from the group consisting of: succinic anhydride, maleic anhydride, glutaric anhydride, malonic acid, succinic acid, maleic acid, and glutaric acid, and mixtures thereof.

19. The dispersant of claim 1 wherein said dispersant comprises one or more compounds having the formula:

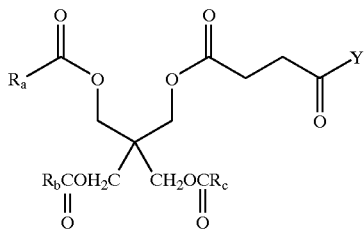

wherein $R_a$ is at least one hydrocarbyl group having up to 50 carbon atoms; $R_b$ is at least one hydrocarbyl group and is not hydrogen; $R_c$ is at least one hydrocarbyl group and is not hydrogen; Y is a polyamine having up to 10 nitrogen atoms.

20. The dispersant of claim 1 wherein the reaction product is produced by the following reaction steps:
   a) reacting said at least one hydrocarbon carboxylic acid with said at least one polyol or partially esterified polyol to form an ester/alcohol reaction product;
   b) reacting said ester/alcohol reaction product with said amine carrier to form an ester linkage between the ester/alcohol reaction product and the amine carrier; and
   c) reacting said polyamine with said amine carrier to form an amide linkage between the polyamine and the amine carrier; thereby forming the dispersant.

21. The dispersant of claim 1 wherein the reaction product is produced by the following reaction steps:
   a) reacting said at least one hydrocarbon carboxylic acid with said polyol or partially esterified polyol to form an ester/alcohol reaction product;
   b) reacting said polyamine with said amine carrier to form an amide reaction product having an amide linkage between the polyamine and the amine carrier and having at least one free carboxylic acid group; and
   c) reacting said ester/alcohol reaction product with said free carboxylic acid group of said amide reaction product to form an ester linkage between the ester/alcohol reaction product and the amine carrier; thereby forming the dispersant.

22. The method of claim 6 wherein said at least one polyol is selected from the group consisting of: neopentyl glycol, 2,2-dimethylol butane, trimethylol ethane, trimethylol propane, trimethylol butane, mono-pentaerythritol, di-pentaerythritol, and tri-pentaerythritol and mixtures thereof.

23. The method of claim 6 wherein said at least one polyamine is selected from the group consisting of: polyamines containing 2 to 5 nitrogen atoms, piperazines, morpholines, anilines, piperidines, and pyrrolidines, and mixtures thereof.

24. The method of claim 6 wherein the hydrocarbon carboxylic acid is selected from the group consisting of: linear, branched, cyclic, and aromatic acids having up to 18 carbon atoms and mixtures thereof.

25. The method of claim 6 wherein the method is performed according to the following steps:
   (a) said at least one hydrocarbon carboxylic acid is reacted with said at least one polyol or partially esterified polyol to form an ester/alcohol reaction product;
   (b) said ester/alcohol reaction product is reacted with said at least one amine carrier to form a reaction product having at least two ester linkages;
   (c) said reaction product having at least two ester linkages is reacted with said polyamine to form the dispersant additive.

26. The method of claim 25 wherein step (a) is performed in the presence of a catalytic amount of p-toluenesulfonic acid.

27. The method of claim 25 further comprising activating the reaction product having at least two ester linkages before step (c).

28. The method of claim 27 wherein ethyl chloroformate is used for said activating step is carried out by treating said reaction product with ethyl chloroformate.

29. The method of claim 25 wherein said at least one hydrocarbon carboxylic acid comprises isononanoic acid.

30. The method of claim 6 wherein the method is performed according to the following steps:
   (a) said at least one amine carrier is reacted with said at least one polyamine to form an amide reaction product, wherein said amide reaction product has a free carboxylic acid group;
   (b) said at least one hydrocarbon carboxylic acid is reacted with said polyol or partially esterified polyol to form an ester/alcohol reaction product; and
   (c) said ester/alcohol reaction product is reacted with said amide reaction product to form the dispersant.

31. The method of claim 30 wherein step (b) is performed in the presence of a catalytic amount of p-toluenesulfonic acid.

32. The method of claim 30 wherein step (c) is performed in the process of a catalytic amount of p-toluenesulfonic acid.

33. The method of claim 30 wherein said at least one hydrocarbon carboxylic acid comprises stearic acid.

34. A method of making a lubricant composition comprising solubilizing the dispersant of claim 1 in a polyol ester base stock to form a lubricant composition, wherein the dispersant comprises about 0.5 to 10% by weight of the lubricant composition.

35. The method of claim 34 wherein the dispersant comprises about 1 to 5% by weight of the lubricant composition.

36. The method of claim 34 further comprising the step of adding to the polyol ester base stock at least one additive selected from the group consisting of: antioxidants, antiwear agents, extreme pressure additives, antifoamants, detergents, hydrolytic stabilizers, metal deactivators, corrosive inhibitors, pour point depressants, and viscosity and viscosity index improvers.

37. A compound having the formula:

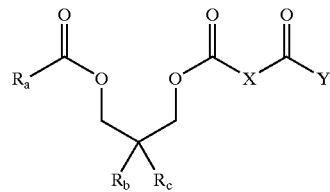

wherein $R_a$ is a hydrocarbyl group containing up to 50 carbon atoms; $R_b$ is a hydrocarbyl group and is not hydrogen; $R_c$ is a hydrocarbyl group and is not hydrogen; X is a hydrocarbyl group having up to 16 carbon atoms; and Y is an amine group having up to 10 nitrogen atoms.

38. The compound of claim 37 wherein $R_a$ is selected from the group consisting of:
—$CH_3$,
—$CH_2CH_3$,
—$CH_2CH_2CH_2CH_3$,
—$CH_2CH(CH_3)_2$,
—$C(CH_3)_3$,
—$CH_2CH_2CH_2CH_2CH_3$,
—$CH_2CH_2CH(CH_3)_2$,
—$CH_2CH_2CH_2CH_2CH_2CH_3$,
—$CH_2CH_2CH_2CH(CH_3)_2$,
—$CH_2CH_2C(CH_3)_3$,
—$CH_2CH_2CH_2CH_2CH_2CH_2CH_3$,
—$CH_2CH_2CH_2CH_2CH(CH_3)_2$,
—$CH_2CH_2CH_2C(CH_3)_3$,
—$CH_2CH_2CH_2CH_2CH_2CH_2CH_2CH_3$,
—$CH_2CH_2CH_2CH_2CH_2CH(CH_3)_2$,
—$CH_2CH_2CH_2CH_2C(CH_3)_3$,
—$CH_2CH(CH_3)CH_2C(CH_3)_3$,
—$CH(CH_2CH_3)CH_2CH_2CH_2CH_3$,
—$CH_2CH_2CH_2CH_2CH_2CH_2CH_2CH_2CH_3$,
—$CH_2CH_2CH_2CH_2CH_2CH_2CH(CH_3)_2$,
—$CH_2CH_2CH_2CH_2CH_2C(CH_3)_3$,
—$CH_2(CH_2)_{15}CH_3$,
—$C_6H_5$,
—$C_6H_{10}$,
—$CH_2CH_2CH_2CH_2COOH$,
—$CH_2CH_2CH_2CH_2CH_2COOH$,
—$CH_2CH_2CH_2CH_2CH_2CH_2COOH$, and
—$CH_2CH_2CH_2CH_2CH_2CH_2CH_2CH_2CH_2CH_2COOH$.

39. The compound of claim 37 wherein $R_b$ and $R_c$ are independently selected from the group consisting of:
—$CH_3$,
—$CH_2CH_3$,
—$CH_2CH_2CH_3$,
—$CH_2OH$, and esters thereof,
—$CH_2OCH_2C(CH_2OH)_3$, and esters thereof,
—$CH_2OCH_2C(CH_2OH)_2CH_2OCH_2C(CH_2OH)_3$, and esters thereof, and mixtures thereof.

40. The compound of claim 37 wherein $R_b$ and $R_c$ are independently selected from the group consisting of: alkyl, cyclo-alkyl, aliphatic, cyclo-aliphatic, and aromatic groups, and mixtures thereof.

41. The compound of claim 37 wherein $R_b$ and optionally $R_c$ further comprise at least one of the following heteroatoms: chlorine, nitrogen, and oxygen.

42. The compound of claim 37 wherein said compound contains at least one oxyalkylene group.

43. The compound of claim 37 wherein said compound contains at least one polyether polyol group.

44. The compound of claim 37 wherein Y is selected from the group consisting of:
—$NHCH_2CH_2NH_2$,
—$NHCH_2CH_2NHCH_2CH_2NH_2$,
—$NHCH_2CH_2NHCH_2CH_2NHCH_2CH_2NH_2$,
—$NHCH_2CH_2NHCH_2CH_2NHCH_2CH_2NHCH_2CH_2NH_2$,
—$NH(CH_2)_3NH(CH_2)_3NH_2$,
—$NH(CH_2)_3NH(CH_2)_3NH(CH_2)_3NH_2$,

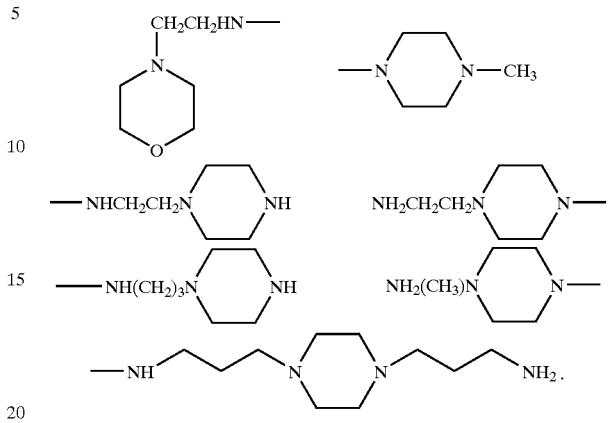

45. The compound of claim 37 wherein Y is selected from the group consisting of:

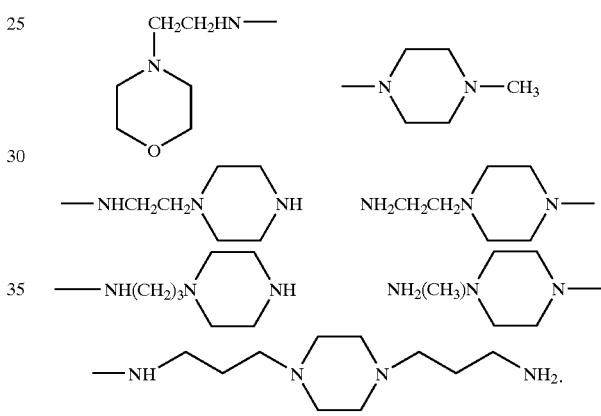

46. The compound of claim 37 wherein X is selected from the group consisting of:
—$CH_2$—,
—$HC=CH$—,
—$CH_2CH_2$—, and
—$CH_2CH_2CH_2$—.

47. A lubricant composition comprising:
a major amount of a polyol ester base stock; and
a dispersant effective amount of the compound of claim 37.

48. The lubricant composition of claim 47 wherein the compound and the polyol ester base stock have the same polyol functional group.

49. The lubricant composition of claim 47 wherein said polyol ester base stock is the product of a reaction of at least one polyol comprising (i) from 4 to 7 carbon atoms and (ii) from 2 to 4 esterifiable hydroxyl groups, with a mixture of $C_5$–$C_{10}$ acids, to form ester/alcohol reaction products.

50. The lubricant composition of claim 47 wherein $R_a$ is selected from the group consisting of:
—$CH_3$,
—$CH_2CH_3$,
—$CH_2CH_2CH_2CH_3$,
—$CH_2CH(CH_3)_2$,
—$C(CH_3)_3$, —CH₂CH₂CH₂CH₂CH₃,
—CH₂CH₂CH(CH₃)₂,
—CH₂CH₂CH₂CH₂CH₂CH₃,
—CH₂CH₂CH₂CH(CH₃)₂,
—CH₂CH₂C(CH₃)₃,
—CH₂CH₂CH₂CH₂CH₂CH₂CH₃,
—CH₂CH₂CH₂CH₂CH(CH₃)₂,
—CH₂CH₂CH₂C(CH₃)₃,
—CH₂CH₂CH₂CH₂CH₂CH₂CH₂CH₃,
—CH₂CH₂CH₂CH₂CH₂CH(CH₃)₂,
—CH₂CH₂CH₂CH₂C(CH₃)₃,
—CH₂CH(CH₃)CH₂C(CH₃)₃,
—CH(CH₂CH₃)CH₂CH₂CH₂CH₃,
—CH₂CH₂CH₂CH₂CH₂CH₂CH₂CH₂CH₃,
—CH₂CH₂CH₂CH₂CH₂CH₂CH(CH₃)₂,
—CH₂CH₂CH₂CH₂CH₂C(CH₃)₃,
—CH₂(CH₂)₁₅CH₃,
—C₆H₅,
—C₆H₁₀,
—CH₂CH₂CH₂CH₂COOH,
—CH₂CH₂CH₂CH₂CH₂COOH,
—CH₂CH₂CH₂CH₂CH₂CH₂COOH, and
—CH₂CH₂CH₂CH₂CH₂CH₂CH₂CH₂CH₂CH₂COOH.

51. The compound of claim 47 wherein R_b and R_c are independently selected from the group consisting of:
—CH₃,
—CH₂CH₃,
—CH₂CH₂CH₃,
—CH₂OH, and esters thereof,
—CH₂OCH₂C(CH₂OH)₃, and esters thereof,
—CH₂OCH₂C(CH₂OH)₂CH₂OCH₂C(CH₂OH)₃, and esters thereof, and mixtures thereof.

52. The compound of claim 47 wherein Y is selected from the group consisting of:
—NHCH₂CH₂NH₂,
—NHCH₂CH₂NHCH₂CH₂NH₂,
—NHCH₂CH₂NHCH₂CH₂NHCH₂CH₂NH₂,
—NHCH₂CH₂NHCH₂CH₂NHCH₂CH₂NHCH₂CH₂NH₂,
—NH(CH₂)₃NH(CH₂)₃NH₂,
—NH(CH₂)₃NH(CH₂)₃NH(CH₂)₃NH₂,

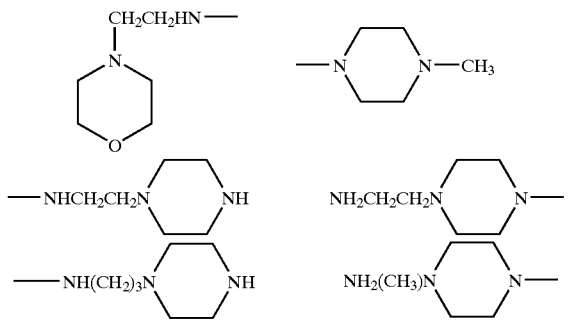

-continued

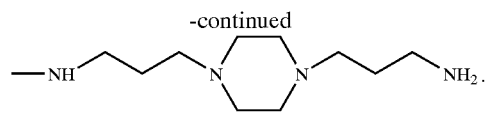

53. A lubricant composition comprising:
a major portion of a polyol ester base stock; and
a minor portion of the dispersant of claim 1.

54. The lubricant composition of claim 53 wherein at least one polyol for forming the dispersant is selected from the group consisting of: neopentyl glycol, 2,2-dimethylol butane, trimethylol ethane, trimethylol propane, trimethylol butane, mono-pentaerythritol, and mixtures thereof.

55. The lubricant composition of claim 53 wherein the polyol ester base stock is the product of a process using an acid mixture comprising C₅ acids, i-C₉ acids, and linear C₇, C₈ and C₁₀ acids.

56. The lubricant composition of claim 53 wherein said dispersant is present in an amount of from about 0.5 wt % to about 10 wt %, and wherein said polyol ester base stock is present in an amount of from about 90 wt % to about 99.5 wt %.

57. The lubricant composition of claim 55 wherein said dispersant is present in an amount of from about 1 wt % to about 5 wt %.

58. The lubricant composition of claim 53, further comprising at least one additive selected from the group consisting of: antioxidants, antiwear agents, extreme pressure additives, antifoamants, detergents, hydrolytic stabilizers, metal deactivators, corrosive inhibitors, pour point depressants, and viscosity and viscosity index improvers.

59. An additive package for a lubricating oil, said additive package comprising:
the dispersant of claim 1; and
one or more additives selected from the group consisting of antioxidants, antiwear agents, extreme pressure additives, antifoamants, detergents, hydrolytic stabilizers, metal deactivators, and corrosive inhibitors.

60. A method of treating a polyol ester to enhance cleanliness, said method comprising reacting the following components to form a reaction product:
(i) at least one polyol ester;
(ii) at least one amine carrier; and
(iii) at least one polyamine;
wherein the reaction product has at least two ester linkages.

61. The method of claim 60 wherein the polyol ester has a hydroxyl number of about 37.

62. The method of claim 60 wherein the polyol ester is present in a major portion.

63. The method of claim 60 wherein the polyol ester is reacted with an amount of a compound of said at least one amine carrier and said at least one polyamine effective to improve the dispersancy of the polyol ester whereby a separate dispersant additive is not needed.

* * * * *